United States Patent [19]

Kageyama

[11] Patent Number: 5,380,910
[45] Date of Patent: Jan. 10, 1995

[54] METHOD FOR PRODUCING AN ASYMMETRIC BIARYL DERIVATIVE

[75] Inventor: Hiroyuki Kageyama, Shizuoka, Japan

[73] Assignee: Ihara Chemical Industry Co., Ltd., Tokyo, Japan

[21] Appl. No.: 38,861

[22] Filed: Mar. 29, 1993

[30] Foreign Application Priority Data

Apr. 28, 1992 [JP] Japan .................................. 4-136251

[51] Int. Cl.$^6$ .................................................. C07C 255/00
[52] U.S. Cl. ...................................... 558/359; 558/411; 560/8
[58] Field of Search ...................... 558/359, 411; 560/8

[56] References Cited

U.S. PATENT DOCUMENTS

| 3,644,477 | 2/1972 | Onsager | 558/359 |
| 4,400,566 | 8/1983 | Colon | 558/359 |
| 4,990,647 | 2/1991 | Himmler et al. | 558/414 |

FOREIGN PATENT DOCUMENTS

| 0131936 | 1/1985 | European Pat. Off. |
| 0341514 | 11/1989 | European Pat. Off. |
| 0376856 | 7/1990 | European Pat. Off. |
| 0470794 | 2/1992 | European Pat. Off. |
| 858514 | 1/1961 | United Kingdom | 558/359 |

OTHER PUBLICATIONS

Journal of Organic Chemistry, vol. 48, No. 25, Mar. 24, 1983, pp. 4904–4907, C. S. Chao, et al. "New Method For The Preparation Of Activated Nickel And Cobalt Powders And Their Application In Biaryl Synthesis".
Patent Abstracts of Japan, vol. 16, No. 194 (C–938), May 11, 1992, JP-A-40 29 957, Jan. 31, 1992.
Beilsteins Handbuch Der Organischen Chemie, 4th Edition, 3rd Supplement, vol. 9, part 4, 1971, pp. 3323–3324, Hans-G Boit.

*Primary Examiner*—Asok Pal
*Attorney, Agent, or Firm*—Oblon, Spivak, McClelland, Maier & Neustadt

[57] ABSTRACT

A method for producing an asymmetric biaryl derivative which comprises dehalogenocoupling halogenated benzene derivatives, wherein a bromobenzene derivative of the formula:

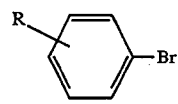

(I)

wherein R is a lower alkyl group or a lower alkoxy group, which is attached at the 3- or 4-position, and a 2-chlorobenzene derivative of the formula:

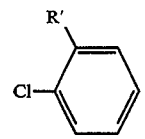

(II)

wherein R' is a cyano group or an alkoxycarbonyl group, are reacted in pyridine in the presence of triphenylphosphine, an anhydrous nickel compound and a reducing metal to obtain an asymmetric biaryl derivative of the formula:

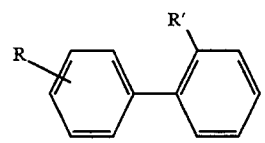

(III)

wherein R and R' are as defined above, and R is attached at the 3- or 4-position.

15 Claims, No Drawings

METHOD FOR PRODUCING AN ASYMMETRIC BIARYL DERIVATIVE

The present invention relates to a method for producing an asymmetric biaryl derivative which is useful as a starting material for liquid crystal polymers or as an intermediate for pharmaceuticals.

Heretofore, a method for producing a biaryl derivative has been disclosed which comprises dehalogenocoupling halogenated aryls in the presence of a reducing agent by means of a nickel compound as a catalyst (Japanese Unexamined Patent Publications No. 15036/1990 and No. 29957/1992).

However, such a method had a problem in the selectivity of the reaction for an asymmetric biaryl derivative.

It is an object of the present invention to provide a method for producing an asymmetric biaryl derivative highly selectively.

The present inventors have conducted extensive researches for an industrial method for producing an asymmetric biaryl derivative highly selectively and as a result, have unexpectedly found it possible to obtain an asymmetric biaryl derivative under such a high selectivity that has never been accomplished before, by a combination of a bromobenzene derivative and a 2-chlorobenzene derivative as starting materials and by using pyridine as the solvent. The present invention has been accomplished on the basis of this discovery.

Thus, the present invention provides a method for producing an asymmetric biaryl derivative which comprises dehalogenocoupling halogenated benzene derivatives, wherein a bromobenzene derivative of the formula:

(I)

wherein R is a lower alkyl group or a lower alkoxy group, which is attached at the 3- or 4-position, and a 2-chlorobenzene derivative of the formula:

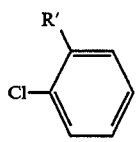
(II)

wherein R' is a cyano group or an alkoxycarbonyl group, are reacted in pyridine in the presence of triphenylphosphine, an anhydrous nickel compound and a reducing metal to obtain an asymmetric biaryl derivative of the formula:

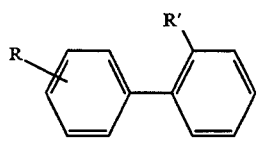
(III)

wherein R and R' are as defined above, and R is attached at the 3- or 4-position.

Now, the present invention will be described in detail with reference to the preferred embodiments.

The bromobenzene derivative of the formula (I) to be used as a starting material in the method of the present invention, may be any such derivative so long as it is a bromobenzene derivative having a $C_{1-6}$ linear or branched alkyl group or a $C_{1-6}$ linear or branched alkoxy group attached at the 3- or 4-position.

Such a bromobenzene derivative may, for example, be 3-bromotoluene, 4-bromotoluene, 3-bromoethylbenzene, 4-bromoethylbenzene, 3-bromopropylbenzene, 4-bromopropylbenzene, 4-bromoisopropylbenzene, 3-bromobutylbenzene, 4-bromobutylbenzene, 4-bromoisobutylbenzene, 3-bromoanisole, 4-bromoanisole, 3-bromoethoxybenzene, 4-bromoethoxybenzene, 3-bromopropoxybenzene, 4-bromopropoxybenzene or 4-bromoisopropoxybenzene.

The 2-chlorobenzene derivative of the formula (II) to be used as another starting material in the method of the present invention, may, for example, be 2-chlorobenzonitrile or a 2-chlorobenzoic acid ester derivative.

When the 2-chlorobenzoic acid ester derivative is used, the alkoxy moiety constituting the alkoxycarbonyl structure may be any alkoxy moiety so long as it is derived from a $C_{1-6}$ alkyl alcohol or an aryl alcohol. Such a 2-chlorobenzoic acid ester derivative may, for example, be methyl 2-chlorobenzoate, ethyl 2-chlorobenzoate, propyl 2-chlorobenzoate, butyl 2-chlorobenzoate, hexyl 2-chlorobenzoate, benzyl 2-chlorobenzoate, isobutyl 2-chlorobenzoate or isopropyl 2-chlorobenzoate.

The molar ratio of the bromobenzene derivative of the formula (I) to the 2-chlorobenzene derivative of the formula (II) to be used in the method of the present invention, is preferably about 1:1, since if either one is in excess, such will not serve to increase the selectivity of the desired product in the reaction.

The anhydrous nickel compound to be used as a catalyst in the method of the present invention, may, for example, be an organic or inorganic anhydrous nickel compound. More specifically, the inorganic anhydrous nickel compound may, for example, be a nickel halide or nickel carbonate, and the organic anhydrous nickel compound may, for example, be a nickel acetate compound. Among them, it is particularly preferred to use an anhydrous nickel halide compound such as anhydrous nickel chloride or anhydrous nickel bromide.

The anhydrous nickel compound is used usually in an amount of at least 0.001, preferably within a range of from 0.005 to 0.1, in a molar ratio to the sum of the molar amounts of the bromobenzene derivative of the formula (I) and the 2-chlorobenzene derivative of the formula (II) as starting materials.

In the method of the present invention, triphenylphosphine is used as a ligand for the nickel catalyst. The triphenylphosphine is used in an amount of from 1 to 5, preferably 2, in a molar ratio to the anhydrous nickel compound. In this case, it is unnecessary to separately prepare a nickel phosphine complex.

The reducing metal to be used in the method of the present invention, may be zinc, manganese or magnesium. Among them, zinc in a fine powder form is preferred.

The reducing metal is used in an amount of at least 0.5, preferably at least 1.0, in a molar ratio to the sum of the molar amounts of the bromobenzene derivative of the formula (I) and the 2-chlorobenzene derivative of the formula (II) as starting materials.

The pyridine to be used as a solvent in the method of the present invention, is preferably dry pyridine. The pyridine is used in an amount of from 100 to 3000 ml, preferably from 300 to 1000 ml, per mol of the sum of the molar amounts of the bromobenzene derivative of the formula (I) and the 2-chlorobenzene derivative of the formula (II) as starting materials.

With respect to the reaction temperature and the reaction pressure in the method of the present invention, the reaction temperature is usually from 0° to 250° C., preferably from room temperature to 100° C., although it depends upon the reaction pressure, and the reaction pressure is not particularly limited, and the reaction is conducted usually under atmospheric pressure, but may be conducted under reduced pressure or under elevated pressure.

According to the method of the present invention, the asymmetric biaryl derivative of the formula (III) can be obtained at a surprisingly high selectivity exceeding 70% and in good yield by using the combination of the bromobenzene derivative of the formula (I) and the chlorobenzene derivative of the formula (II) as starting material and pyridine as a solvent. Accordingly, the method of the present invention is suitable as an industrial method for producing the asymmetric biaryl derivative.

perature for 30 minutes. The temperature was raised to 80° C., and the mixture was reacted for 6 hours. Then, 400 ml of toluene was added thereto, and the solid was filtered off while it was still hot. The toluene layer was analyzed by gas chromatography. The results are shown in Table 1. Then, pyridine and toluene were recovered under reduced pressure. Then, 500 ml of toluene was added to the residue, and the solid was filtered off while it was still hot and washed with 100 ml of toluene. The warm toluene layer was washed with 300 ml of 5% hydrochloric acid, then with 300 ml of a 5% sodium hydrogencarbonate aqueous solution and further twice with 300 ml of warm water. The toluene layer was concentrated to obtain 54 g of a crude product. This product was distilled to obtain 28.4 g (yield: 57%, purity: 97.4%) of white crystals of 2-cyano-4'-methyl-1,1'-biphenyl.

Further, to confirm the structure, the product was recrystallized from cyclohexane to obtain a sample product for analysis.

Melting point: 49°–50° C. (melting point disclosed in a literature: 48.0°–49.5° C., J. Med. Chem., vol 34, 2525 (1991))

NMR(CDCl$_3$): δ2.4 (3H,s,CH$_3$), 7.8-7.2 (8H,m,ArH)

IR(KBr): 3060, 3020, 2920, 2240, 1600, 1560, 1520, 1480 cm$^{-1}$

TABLE 1

Examples for cross-coupling reactions

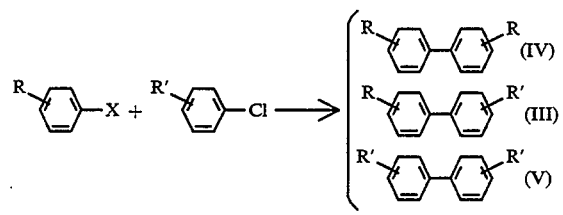

|  | X | R | R' | Solvent | (IV) | (III) | (V) | Selectivity (%) $\frac{III}{(IV + III + V)} \times 100$ |
|---|---|---|---|---|---|---|---|---|
| Example 1 | Br | 4-Me | 2-CN | Py | 11 | 69 | 12 | 75 |
| Example 2 | Br | 4-Me | 2-COOMe | Py | 11 | 59 | 14 | 70 |
| Example 3 | Br | 3-Me | 2-CN | Py | 11 | 64 | 10 | 75 |
| Example 4 | Br | 4-OMe | 2-CN | Py | 11 | 52 | 10 | 71 |
| Comp. Example 1 | Br | 4-Me | 2-CN | DMAc | 11 | 26 | 26 | 41 |
| Comp. Example 2 | Br | 4-Me | 3-CN | Py | 20 | 35 | 13 | 51 |
| Comp. Example 3 | Br | 4-Me | 4-CN | Py | 31 | 19 | 20 | 27 |
| Comp. Example 4 | Br | 2-Me | 2-CN | Py | 6 | 42 | 29 | 55 |
| Comp. Example 5 | I | 4-Me | 2-CN | Py | 21 | 45 | 18 | 54 |
| Comp. Example 6 | Br | 4-OMe | 4-CN | Py | 25 | 22 | 18 | 34 |

Now, the present invention will be described in further detail with reference to Examples. However, it should be understood that the present invention is by no means restricted by such specific Examples.

EXAMPLE 1

Preparation of 2-cyano-4'-methyl-1,1'-biphenyl

Into a 1 l four necked flask, 500 ml of dry pyridine, 44.3 g (0.259 mol) of 4-bromotoluene, 35.6 g (0.259 mol) of 2-chlorobenzonitrile, 3.24 g (0.025 mol) of anhydrous nickel chloride, 13.1 g (0.05 mol) of triphenylphosphine and 67.6 g (1.034 mol) of zinc powder were charged under a nitrogen atmosphere and stirred at room tem- In Table 1, the numerical values in the columns for (IV), (III) and (V) represent total areas % by the gas chromatography analyses; Me in the columns for R and R' represents a methyl group; and Py in the column for solvent represents pyridine, and DMAc represents dimethylacetamide.

Comparative Example 1

Into a 100 ml flask, 50 ml of dry dimethylacetamide, 4.28 g (0.025 mol) of 4-bromotoluene, 3.44 g (0.025 mol) of 2-chlorobenzonitrile, 0.32 g (0.0025 mol) of anhydrous nickel chloride, 2.75 g (0.0105 mol) of triphenylphosphine and 4.90 g (0.075 mol) of zinc powder were charged under a nitrogen atmosphere and stirred at room temperature for 30 minutes. The mixture was heated by an oil bath and reacted at 85° C. for 2 hours. Then, the reaction solution was analyzed by gas chromatography. The results are shown in Table 1.

Comparative Examples 2 and 3

The reaction was conducted in the same manner as in Example 1 except that instead of 2-chlorobenzonitrile used in Example 1, 3-chlorobenzonitrile (Comparative Example 2) or 4-chlorobenzonitrile (Comparative Example 3) was used in the same molar amount as the molar amount of 2-chlorobenzonitrile used in Example 1, and the reaction solution was analyzed by gas chromatography. The results are shown in Table 1.

After completion of the reaction, no residue of the starting material 3-chlorobenzonitrile or 4-chlorobenzonitrile was observed.

Comparative Examples 4 and 5

The reaction was conducted in the same manner as in Example 1 except that instead of 4-bromotoluene used in Example 1, 2-bromotoluene (Comparative Example 4) or 4-iodotoluene (Comparative Example 5) was used in the same molar amount as the molar amount of 4-bromotoluene used in Example 1, and the reaction solution was analyzed by gas chromatography. The results are shown in Table 1.

After completion of the reaction, no residue of the starting material 2-bromotoluene or 4-iodotoluene was observed.

Comparative Example 6

The reaction was conducted in the same manner as in Example 1 except that instead of 4-bromotoluene, 4-bromoanisole was used, and instead of 2-chlorobenzonitrile, 4-chlorobenzonitrile was used, in the same molar amounts as the molar amounts of the respective corresponding compounds used in Example 1, and the reaction solution was analyzed by gas chromatography. The results are shown in Table 1.

After completion of the reaction, no residue of the starting material 4-bromoanisole or 4-chlorobenzonitrile was observed.

EXAMPLE 2

Preparation of methyl 4'-methyl-1,1'-biphenyl-2-carboxylate

Into a 100 ml flask, 50 ml of dry pyridine, 4.28 g (0.025 mol) of 4-bromotoluene, 4.26 g (0.025 mol) of methyl 2-chlorobenzoate, 0.32 g (0.0025 mol) of anhydrous nickel chloride, 1.31 g (0.005 mol) of triphenylphosphine and 4.90 g (0.075 mol) of zinc powder were charged under a nitrogen atmosphere and stirred at room temperature for 30 minutes. The mixture was heated by an oil bath and reacted at 85° C. for 3 hours. The reaction solution was analyzed by gas chromatography. The results are shown in Table 1. The data confirming the structure are shown below.

GC-MS: 226(M+), 195(M+-31)

NMR(CDCl$_3$): δ2.36 (3H,s,CH$_3$), 3.62 (3H,s,OCH$_3$), 7.8-7.2 (8H,m,ArH)

IR(KBr): 1730, 1600, 1520, 1485, 1450, 1435, 1295, 1280, 1250, 1190, 1130, 1090, 1050, 820 cm$^{-1}$

EXAMPLE 3

Preparation of 2-cyano-3'-methyl-1,1'-biphenyl

In the same manner as in Example 2, 3-bromotoluene and 2-chlorobenzonitrile were reacted at 85° C. for 3 hours, and the reaction solution was analyzed by gas chromatography. The results are shown in Table 1.

EXAMPLE 4

Preparation of 2-cyano-4'-methoxy-1,1'-biphenyl

In the same manner as in Example 1, 4-bromoanisole and 2-chlorobenzonitrile were reacted at 85° C. for 5 hours, and the reaction solution was analyzed by gas chromatography. The results are shown in Table 1.

The reaction solution was post-treated to obtain 4.94 g of a crude product. The product was further distilled and recrystallized from a solvent mixture of cyclohexane and chloroform to obtain 2.61 g (purity: 90%) of white crystals of 2-cyano-4'-methoxy-1,1'-biphenyl.

Melting point: 79°-85° C.

GC-MS: 209 (M+)

I claim:

1. A method for producing an asymmetric biaryl compound, which comprises dehalogenocoupling a halogenated benzene compound, wherein a bromobenzene compound of the formula:

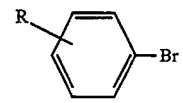

(I)

wherein R is a lower alkyl group or a lower alkoxy group, which is attached at the 3- or 4-position, and a 2-chlorobenzene compound of the formula:

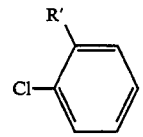

(II)

wherein R' is a cyano group or an alkoxycarbonyl group, are reacted in pyridine in the presence of triphenylphosphine, an anhydrous nickel compound and a reducing metal to obtain an asymmetric biaryl compound of the formula:

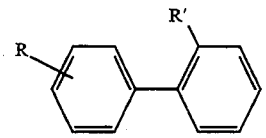

(III)

with a selectivity of at least 70% for said compound of the formula (III), wherein R and R' are as defined above, and R is attached at the 3- or 4-position.

2. The method according to claim 1, wherein the bromobenzene compound of the formula (I) is a bromobenzene compound having a $C_{1-6}$ linear or branched alkyl group or a $C_{1-6}$ linear or branched alkoxy group attached at the 3-or 4-position.

3. The method according to claim 1, wherein the 2-chlorobenzene compound of the formula (II) is 2-chlorobenzonitrile or a 2-chlorobenzoic acid ester.

4. The method according to claim 1, wherein the molar ratio of the bromobenzene compound of the formula (I) to the 2-chlorobenzene compound of the formula (II) is about 1:1.

5. The method according to claim 1, wherein the anhydrous nickel compound is an anhydrous nickel halide, anhydrous nickel carbonate or anhydrous nickel acetate.

6. The method according to claim 1, wherein the anhydrous nickel compound is used in an amount of at least 0.001 in a molar ratio to the sum of the molar amounts of the bromobenzene compound of the formula (I) and the 2-chlorobenzene compound of the formula (II).

7. The method according to claim 1, wherein the triphenylphosphine is used in an amount of from 1 to 5 in a molar ratio to the anhydrous nickel compound.

8. The method according to claim 1, wherein the reducing metal is zinc, manganese or magnesium.

9. The method according to claim 1, wherein the reducing metal is used in an amount of at least 0.5 in a molar ratio to the sum of the molar amounts of the bromobenzene compound of the formula (I) and the 2-chlorobenzene compound of the formula (II).

10. The method according to claim 1, wherein the pyridine is used in an amount of from 100 to 3000 ml per mol of the sum of the molar amounts of the bromobenzene compound of the formula (I) and the 2-chlorobenzene compound of the formula (II).

11. The method according to claim 2, wherein said bromobenzene compound is selected from the group consisting of 3-bromotoluene, 4-bromotoluene, 3-bromoethylbenzene, 4-bromoethylbenzene, 3-bromopropylbenzene, 4-bromopropylbenzene, 4-bromoisopropylbenzene, 3-bromobutylbenzene, 4-bromobutylbenzene, 4-bromoisobutylbenzene, 3-bromoanisole, 4-bromoanisole, 3-bromoethoxybenzene, 4-bromoethoxybenzene, 3-bromopropoxybenzene, 4-bromopropoxybenzene and 4-bromoisopropoxybenzene.

12. The method according to claim 3, wherein said 2-chlorobenzene compound is selected from the group consisting of 2-chlorobenzonitrile, methyl 2-chlorobenzoate, ethyl 2-chlorobenzoate, propyl 2-chlorobenzoate, butyl 2-chlorobenzoate, hexyl 2-chlorobenzoate, benzyl 2-chlorobenzoate, isobutyl 2-chlorobenzoate and isopropyl 2-chlorobenzoate.

13. The method according to claim 8, wherein said reducing metal is zinc in powdered form.

14. The method according to claim 1, wherein said reaction is conducted at a temperature of from about 0° C. to 250° C.

15. The method according to claim 14, wherein said reaction is conducted at a temperature of from room temperature to 100° C.

* * * * *